United States Patent
Ye et al.

(10) Patent No.: US 9,243,019 B2
(45) Date of Patent: Jan. 26, 2016

(54) HYDROXYSAFFLOR YELLOW A SODIUM AND PREPARATION AS WELL AS APPLICATION THEREOF

(71) Applicant: ZHEJIANG YONGNING PHARMACEUTICAL CO LTD, Taizhou, Zhejiang (CN)

(72) Inventors: Fengqi Ye, Zhejiang (CN); Ben Cai, Zhejiang (CN); Min Lu, Zhejiang (CN); Yongling Chen, Zhejiang (CN)

(73) Assignee: ZHEJIANG YONGNING PHARMACEUTICAL CO LTD, Taizhou, Zhejiang Province (CN)

( * ) Notice: Subject to any disclaimer, the term of this patent is extended or adjusted under 35 U.S.C. 154(b) by 0 days.

(21) Appl. No.: 14/383,557

(22) PCT Filed: Jun. 8, 2013

(86) PCT No.: PCT/CN2013/000686
§ 371 (c)(1),
(2) Date: Sep. 6, 2014

(87) PCT Pub. No.: WO2014/121424
PCT Pub. Date: Aug. 14, 2014

(65) Prior Publication Data
US 2015/0025030 A1    Jan. 22, 2015

(30) Foreign Application Priority Data
Feb. 7, 2013   (CN) .......................... 2013 1 0048476

(51) Int. Cl.
*C07H 7/04*    (2006.01)
*C07H 15/207*  (2006.01)
*C07D 309/04*  (2006.01)

(52) U.S. Cl.
CPC ............ *C07H 15/207* (2013.01); *C07D 309/04* (2013.01); *C07H 7/04* (2013.01)

(58) Field of Classification Search
None
See application file for complete search history.

(56) References Cited

FOREIGN PATENT DOCUMENTS

| CN | 1475272 | 2/2004 |
|---|---|---|
| CN | 1895317 | 1/2007 |
| CN | 101168539 | 4/2008 |
| CN | 101195647 | 6/2008 |
| CN | 101215307 | 7/2008 |
| CN | 101879155 | * 11/2010 |
| CN | 102675379 | 9/2012 |

* cited by examiner

*Primary Examiner* — Traviss C McIntosh, III (57) ABSTRACT

A hydroxysafflor yellow A sodium compound as shown in a formula (I) and preparation as well as medicinal application thereof are provided. According to the present invention, the safflower is utilized as a raw material. A monomer pharmaceutical compound, the hydroxysafflor yellow A sodium, is obtained by sufficient processes, and a purity thereof is surely above 98.5%. Therefore, the hydroxysafflor yellow A sodium is a monomer compound, which is safer, more effective, more stable and more controllable than hydroxysafflor yellow A, for treating blood circulation disorders such as platelet aggregation, coronary heart disease, angina pectoris and acute cerebral ischemia. Furthermore, the hydroxysafflor yellow A sodium has sufficient solubility and human tolerance.

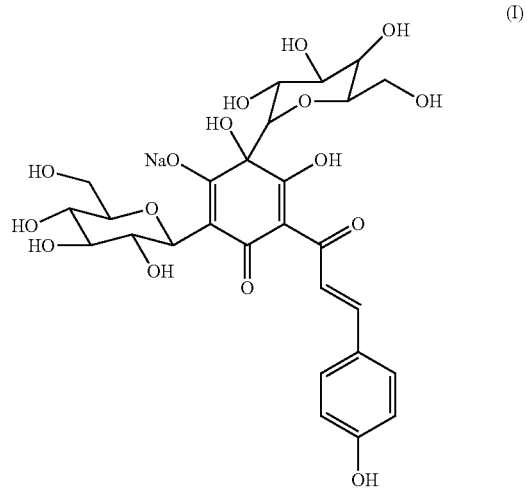

13 Claims, 5 Drawing Sheets fig. 1 fig. 2 fig. 3 fig. 4 fig. 5

HYDROXYSAFFLOR YELLOW A SODIUM AND PREPARATION AS WELL AS APPLICATION THEREOF

CROSS REFERENCE OF RELATED APPLICATION

This is a U.S. National Stage under 35 U.S.C 371 of the International Application PCT/CN2013/000686, filed Jun. 8, 2013, which claims priority under 35 U.S.C. 119(a-d) to CN 201310048476.8, filed Feb. 7, 2013.

BACKGROUND OF THE PRESENT INVENTION

1. Field of Invention

The present invention relates to a compound, and more particularly to a hydroxysafflor yellow A sodium compound, and a preparation method as well as medicinal application thereof. The present invention also relates to a field of natural pharmaceutical chemistry.

2. Description of Related Arts

Chinese medicine safflower is dried flower of *Carthamus tinctouius* L., which is a common Chinese medicine for activating blood and dissipating blood stasis, and is applicable for treating blood circulation disorders such as coronary heart disease and angina pectoris. Hydroxysafflor yellow A is a compound with a mono-chalcone glycoside structure, and is a water-soluble portion of the safflower with the most effective pharmacological effect, which can inhibit platelet aggregation and release induced by platelet activating factors, and competitively inhibit combination of the platelet activating factor and the platelet receptor. Therefore, the hydroxysafflor yellow A is an effective ingredient of the safflor yellow for activating blood and dissipating blood stasis. According to research results, the hydroxysafflor yellow A has many pharmacological effects on cardiovascular such as anticoagulant, promoting fibrinolysis, anti-thrombosis, and improving microcirculation.

The conventional technologies have disclosed the hydroxysafflor yellow A, a various of extraction, separation and purification methods thereof, and hydroxysafflor yellow A injection (comprising freeze-dried powder injection). However, a purity and stability of the conventional hydroxysafflor yellow A products are not sufficient. Judging from the purity of the conventional safflor yellow, the impurity content is basically above 10%. Furthermore, structure and property of the impurity are indefinite, and quality is not completely controllable. And impurity spectrums of the safflor yellow extracted from the safflower are not consistent.

Chinese patent application CN102675379A disclosed a method for extracting refined hydroxysafflor yellow A from safflower, and particularly disclosed five steps: extracting from safflower; purifying by alkalescent ion-exchange resin; purifying by macroporous resin with medium chemical polarity; purifying by nonpolar macroporous resin; and freeze-drying; wherein a content of the hydroxysafflor yellow A is above 80%, a turnover rate is above 20%.

Chinese patent applications CN101195647A, CN101215307A and CN1475272A disclosed a method for extracting refined hydroxysafflor yellow A from safflower, wherein a content of the hydroxysafflor yellow A is above 90%.

However, because stability of the hydroxysafflor yellow A is not sufficient, the purity thereof will decrease after long-time storage, and the medicinal effect is decreased, which leads to medication safety problem of the hydroxysafflor yellow A.

Medicinal research mainly focuses on medicine safety, effectiveness, stability and controllability, none of the four aspects can be omitted. Because the safflor yellow injection produced and clinically utilized is pharmacodynamically tested and clinically evaluated, safety and effectiveness of the hydroxysafflor yellow A compound has been proven. However, due to the extraction process of hydroxysafflor yellow A and compound stability, the impurity content is basically above 10% according to the purity of the raw material of the hydroxysafflor yellow A which is commercially available. Furthermore, structure and property of the impurity are indefinite, and quality is not completely controllable. And impurity spectrums of the safflor yellow extracted from the safflower are not consistent. Therefore, stability and purity of the effective ingredients of the conventional hydroxysafflor yellow A medicine, especially injection, are still the main restrict or influence of safety and improvement of quality controllability.

SUMMARY OF THE PRESENT INVENTION

For overcoming disadvantages of conventional technologies, a compound of hydroxysafflor yellow A is provided according to the present invention. More particularly, a compound of hydroxysafflor yellow A sodium is provided, wherein safflower is utilized as a raw material, the compound is obtained by sufficient processes such as extraction, separation and purification. According to research results, the hydroxysafflor yellow A sodium is safer, more effective, more stable and more controllable than the hydroxysafflor yellow A as a monomer compound, which is applicable for treating blood circulation disorders such as coronary heart disease and angina pectoris.

Accordingly, in order to accomplish the above object, the present invention provides a hydroxysafflor yellow A sodium, as shown in a formula (I).

A molecular formula thereof is: $C_{27}H_{31}O_{16}Na$.

Another object of the present invention is to provide a method for preparing hydroxysafflor yellow A sodium as shown in the formula (I), comprising a step of preparing the hydroxysafflor yellow A sodium as shown in the formula (I) with hydroxysafflor yellow A as shown in a formula (II).

Preferably, the hydroxysafflor yellow A sodium as shown in the formula (I) is prepared with the hydroxysafflor yellow A as shown in the formula (II) by a method comprising a step of: preparing the hydroxysafflor yellow A sodium as shown in the formula (I) with the hydroxysafflor yellow A as shown in the formula (II) by sodion-exchange resin column, or by reaction with a sodium salt; wherein the sodium salt is selected from the group consisting of sodium hydroxide, sodium carbonate and sodium bicarbonate.

Preferably, the sodion-exchange resin is 001*7 sodion-exchange resin or macroporous HB-8 sodion-exchange resin. The above two kinds of resin products are commercially available, e.g., which are able to be purchased from Shanghai Huazhen Sci. & Tech. Co., Ltd.

According to a preferred embodiment, safflower is utilized as a raw material, the hydroxysafflor yellow A sodium as shown in the formula (I) is obtained after extraction, sodium salt transformation, separation and purification, wherein the method particularly comprises steps of:

a) extracting: extracting the safflower with water;

b) transforming to sodium salt: passing extract obtained in the step a) through a sodion-exchange resin column, transforming safflor yellow to the hydroxysafflor yellow A sodium as shown in the formula (I);

c) separating: separating eluant obtained in the step b), which comprises the hydroxysafflor yellow A sodium as shown in the formula (I), by a macroporous adsorbent resin column, obtaining a crude product of the hydroxysafflor yellow A sodium as shown in the formula (I); and d) purifying: separating the crude product obtained in the step c) of the hydroxysafflor yellow A sodium as shown in the formula (I) by dextran gel column chromatography, then filtering with an ultrafiltration membrane, obtaining a refined product of the hydroxysafflor yellow A sodium as shown in the formula (I).

Preferably, in the step a), the safflower is extracted 2~3 times with the water at 50~100° C., wherein a weight of the water is 10~30 times of a weight of the safflower. The safflower is extracted for 0.5~24 h each time, then the extract is collected and cooled.

Preferably, in the step b), the extract obtained in the step a) passes through the sodion-exchange resin column, wherein the sodion-exchange resin is 001*7 sodion-exchange resin or macroporous HB-8 sodion-exchange resin; then the eluant comprising the hydroxysafflor yellow A sodium as shown in the formula (I) is collected;

Preferably, in the step c), the eluant obtained in the step b), which comprises the hydroxysafflor yellow A sodium as shown in the formula (I), is separated by a macroporous adsorbent resin HZ801 column, and water is utilized as an eluting agent, the eluant is collected for obtaining the crude product of the hydroxysafflor yellow A sodium as shown in the formula (I).

Preferably, in the step d), the crude product obtained in the step c) of the hydroxysafflor yellow A sodium as shown in the formula (I) is separated by Sephadex LH-20 dextran gel column chromatography, and pure water is utilized as an eluting agent. The eluant comprising the hydroxysafflor yellow A sodium as shown in the formula (I) is collected and processed with vacuum concentration for obtaining concentrate thereof, then the concentrate is ultrafiltered by an ultrafiltration membrane with molecular weight cut-off of 8000~10000 daltons for obtaining ultrafiltrate, the refined product of the hydroxysafflor yellow A sodium as shown in the formula (I) is obtained after freeze-drying.

According to another embodiment, safflower is utilized as a raw material, the hydroxysafflor yellow A sodium is obtained after extraction, separation, purification, acidization and sodium salt transformation, wherein the method particularly comprises steps of:

a) extracting: extracting the safflower with water for obtaining extract thereof;

b) separating: separating the eluant of the safflower obtained in the step a) by a macroporous adsorbent resin column, obtaining a crude product of the safflor yellow;

c) purifying: separating the crude product of the safflor yellow obtained in the step b) by dextran gel column chromatography, then filtering with an ultrafiltration membrane, freeze-drying for obtaining a refined product of the safflor yellow;

d) acidizing: adding water to the refined product of the safflor yellow, adding acid (preferably hydrochloric acid) for adjusting a pH value to 1.5~2.5, collecting pale yellow solid separated out for obtaining hydroxysafflor yellow A as shown in the formula (II); and e) transforming to sodium salt: adding water to the hydroxysafflor yellow A obtained in the step d), which is shown in the formula (II), and adjusting the pH value to 6 with 0.1 mol/L~10 mol/L sodium hydroxide, sodium carbonate or sodium bicarbonate (preferably sodium hydroxide), transforming the hydroxysafflor yellow A as shown in the formula (II) to the hydroxysafflor yellow A sodium as shown in the formula (I), filtering with an ultrafiltration membrane, and freeze-drying filtrate for obtaining a refined product of the hydroxysafflor yellow A sodium as shown in the formula (I).

Preferably, the macroporous adsorbent resin column is HSZ801 macroporous adsorbent resin. Preferably, the dextran gel column chromatography comprises Sephadex LH-20 dextran gel column chromatography for separating, and pure water as an eluting agent; an ultrafiltration membrane with molecular weight cut-off of 8000~10000 daltons for ultrafiltering.

The water extract of the safflower mainly comprises the safflor yellow. The present invention surprisingly found that when the water extract of the safflower passes through the sodion-exchange resin column (such as the 001*7 sodion-exchange resin and macroporous HB-8 sodion-exchange resin), all the safflor yellow in the water extract of the safflower will be transformed to the compound of the hydroxysafflor yellow A sodium as shown in the formula (I). According to speculation of the inventor, during the separation processed by the sodion-exchange resin, free anionic of the hydroxysafflor yellow A as shown in the formula (II) of the safflor yellow is combined with sodion exchanged out, and forms the hydroxysafflor yellow A sodium as shown in the formula (I). The speculation is experimentally verificated as follows. A sample comprising the hydroxysafflor yellow A sodium as shown in the formula (I) is separated with the 001*7 sodion-exchange resin according to the method in the preferred embodiment 1 of the present invention, and eluant is collected, wherein a testing result shows that the hydroxysafflor yellow A sodium as shown in the formula (I) exists.

Similarly, the present invention also found that, the hydroxysafflor yellow A can be prepared by: acidizing the refined product of the safflor yellow, then reacting with sodium salt such as sodium hydroxide, sodium carbonate and sodium bicarbonate. With the above method, the compound of the hydroxysafflor yellow A sodium as shown in the formula (I) is also able to be prepared with a high yield and a high purity.

Another object of the present invention is to provide a pharmaceutic preparation, comprising hydroxysafflor yellow A sodium as shown in the formula (I) as an active ingredient and a pharmaceutically acceptable carrier; preferably, the pharmaceutic preparation is a freeze-dried injection; the freeze-dried injection is prepared by dissolving the hydroxysafflor yellow A sodium as shown in the formula (I), or a refined product of the hydroxysafflor yellow A sodium as shown in the formula (I) prepared by the above methods, in injection water, then packing in bottles after filtered by a 0.22 μm macroporous filtering membrane or an ultrafiltration membrane with molecular weight cut-off of 8000~10000 daltons, and freeze-drying for obtaining the freeze-dried injection of the hydroxysafflor yellow A sodium as shown in the formula (I).

A content of the hydroxysafflor yellow A sodium is 50~200 mg per unit dosage. For example, the hydroxysafflor yellow A sodium is able to be prepared as: a) a freeze-dried injection of the hydroxysafflor yellow A sodium for injection use, and a content of the hydroxysafflor yellow A sodium is 50~200 mg per bottle; b) a sodium chloride injection of the hydroxysafflor yellow A sodium, and a content of the hydroxysafflor yellow A sodium is 50~200 mg per 100 ml sodium chloride; and c) a glucose injection of the hydroxysafflor yellow A sodium, and a content of the hydroxysafflor yellow A sodium is 50~200 mg per 100 ml glucose injection.

According to another preferred embodiment of the present invention, hydroxysafflor yellow A sodium as shown in the formula (I) and a freeze-dried injection thereof are provided, which are prepared by extracting the safflower, transforming by sodion-exchange resin, separating by macroporous resin, separating by dextran gel chromatography and ultrafiltering, wherein the preparation method particularly comprises steps of:

a) utilizing the safflower as a raw material, adding water with a temperature of 50~100° C. for extraction, wherein the safflower is extracted 2~3 times and 0.5~24 h each time, a weight of the water is 10~30 times of a weight of the safflower; filtering out dregs after extraction, cooling to 5~30° C., and waiting for 2~24 h;

b) passing the extract through the sodion-exchange resin, wherein a flow rate is 1~30 ml/min; then discharging the extract from a column with water, wherein a volume of the water equals to a volume of the column;

c) separating by macroporous adsorbent resin: separating the safflower extract obtained in the step b) by a macroporous adsorbent resin HZ801 column, wherein a ratio of an internal diameter and a height thereof is 1:8~15; utilizing pure water as an eluting agent, wherein an eluting speed is 10~30 ml/min; collecting eluant thereof, processing with vacuum concentration for obtaining a crude concentrate of the hydroxysafflor yellow A sodium;

d) separating with the dextran gel chromatography: separating the crude concentrate of the hydroxysafflor yellow A sodium obtained in the step c) by Sephadex LH-20 dextran gel chromatography after filtration or centrifugation, wherein a ratio of a diameter and a height of a chromatography column is 1:5~20; utilizing the pure water as the eluting agent, wherein the eluting speed is 1~10 ml/min; collecting eluant of the hydroxysafflor yellow A sodium, processing with vacuum concentration for obtaining concentrate thereof;

e) ultrafiltering: ultrafiltering the concentration obtained in the step d) by an ultrafiltration membrane with molecular weight cut-off of 8000~10000 daltons after filtration or centrifugation, and obtaining ultrafiltrate;

f) freeze-drying: freeze-drying the ultrafiltrate obtained in the step e) for obtaining the hydroxysafflor yellow A sodium; and g) dissolving the refined product of the hydroxysafflor yellow A sodium obtained in the step f) in injection water, then packing in bottles after filtered by a 0.22 μm macroporous filtering membrane or the ultrafiltration membrane with the molecular weight cut-off of 8000~10000 daltons, and freeze-drying for obtaining the freeze-dried injection of the hydroxysafflor yellow A sodium;

wherein the sodion-exchange resin is 001*7 sodion-exchange resin or macroporous HB-8 sodion-exchange resin; the macroporous resin separation utilizes macroporous adsorbent resin HZ801; the dextran gel column chromatography separation utilizes dextran gel column chromatography LH-20; the ultrafiltration utilizes the ultrafiltration membrane with the molecular weight cut-off of 8000~10000 daltons.

The present invention also provides application of the hydroxysafflor yellow A sodium, as shown in the formula (I), in medicine preparation, wherein the medicine has an effect of preventing platelet aggregation induced by PAF or ADP, so as to prevent and treat a disease caused by myocardial ischemia, cerebral ischemia or thrombosis. A clinical dosage thereof is 50~200 mg per day.

According to the present invention, the safflower is utilized as the raw material. The monomer pharmaceutical compound, the hydroxysafflor yellow A sodium as shown in the formula (I), is obtained by sufficient processes, and a purity thereof is surely above 98.5%. According to the present invention, the hydroxysafflor yellow A sodium is more stable and more conducive to safety and controllability of the medicine. Therefore, the hydroxysafflor yellow A sodium is a monomer compound, which is safer, more effective, more stable and more controllable than the hydroxysafflor yellow A, for treating blood circulation disorders such as coronary heart disease and angina pectoris.

Pharmacodynamics Experiment 1:

Object: observing effects of preventing acute myocardial infarction provided by the hydroxysafflor yellow A sodium and safflor yellow injection (50 mg/bottle) which is intravenously injected on dogs.

Medicine Tested:

safflor yellow injection (50 mg/bottle); purchased from: Zhejiang Yongning Pharma Co., Ltd; content: 42.5 mg the hydroxysafflor yellow A per 50 mg/bottle; and freeze-dried powder of the hydroxysafflor yellow A sodium (prepared in the preferred embodiment 1).

Animal:

18 healthy mongrels, half male and half female, randomly divided into three groups.

| Group | Quantity | Dosage | Injection method |
|---|---|---|---|
| Saline | 6 | 1 ml/kg | Intravenous injection |
| Safflor yellow injection | 6 | 10 mg/kg | Intravenous injection |
| Hydroxysafflor yellow A sodium | 6 | 10 mg/kg | Intravenous injection |

The above medicines were all intravenously injected, which was in accordance with a clinical application method (intravenous injection), wherein the intravenous injection was provided once.

Experiment Method

Intravenously anaesthetizing the animal with 3% pentobarbital sodium after weighing, wherein a dosage was 30 mg/kg; processing with trachea cannula, then connecting to an anesthesia ventilator and processing with thoracotomy for mechanical ventilation, wherein a respiratory frequency was 16~18 times/min, a ratio of inspiratory and expiratory volume was 1:2, tidal volume was 350~550 ml, and ventilation indexes were adjusted according to results of blood gas analysis; subcutaneously inserting needle electrodes into four limbs and chest, monitoring standard limb leads and V1, V3 and V5 electrocardiograms; processing with thoracotomy along a third intercostals space of left sternal border, and cutting off a fourth rib for fully exposing a heart; cutting open pericardium and processing with pericardium hammock; intravenously injecting lidocaine with a dosage of 2 mg/kg for preventing arrhythmia; separating a left anterior descending initial portion of coronary artery, providing a first loose knot and a second loose knot by twining two sections of No. 1 silk at an anterior descending artery, inserting a steel wire with a diameter of 1 mm into the first loose knot, ligating the first knot, wherein the steel wire was ligated with the coronary artery, then drawing out the steel wire; ingating the senond knot after 30 minutes (intravenously injecting the medicine to be tested at the same time); observing changes of the electrocardiograph 5 min, 10 min, 30 min, 1 h, 2 h, 3 h and 4 h after ligating the second knot; taking the heart out after 4 h and weighting the whole heart, pressing 10 ml 10% carbon ink along openings of left and right coronary arteries at aortic root for displaying non-ischemic myocardium (dyed black) and ischemic myocardium (not dyed black), cutting the ischemic myocardium for weighting; then cutting the ischemic myocardium into 0.5~1 cm thick myocardium sheets and washing with the saline, dyeing in 0.025% nitro blue tetrazolium (NBT) at 37° C.; shaking the NBT during dyeing for fully contacting with the myocardium; washing unnecessary NBT right after 30 min; wherein infarcted myocardium was not dyed, non-infarcted myocardium was dyed black, cutting off the dyed part and weighing the non-dyed part.

Observation Index

Main observation indexes after injection are ST segment elevation of precordial electrocardiograph, myocardial infarction range, etc., which are as follows.

a) ST segment elevation: $\Delta ST$, wherein the ST before ligation is a 0 point;

observation time is 5 min, 10 min, 30 min, 1 h, 2 h, 3 h and 4 h after injection.

b) myocardial infarction degree the weight of ischemic myocardium (g): a weight of blood-supplying myocardium of the ligated coronary artery;

the weight of infarcted myocardium (g): a weight of non-dyed myocardium;

myocardial infarction rate (%): (the weight of ischemic myocardium/the weight of infarcted myocardium)*100%.

Comparison

A negative comparison group with the saline was provided, wherein a dosage was 1 mg/kg.

Analysis

Experimental results are shown in a form of $X \pm S$, and were processed with unpaired t-test statistics, wherein $P<0.05$ represents significant statistical difference.

Experimental Results a) influence of the medicine on the ST segment elevation of the anesthetized dog after death caused by myocardial infarction.

Compared to the saline group, the ST segment elevation caused by anesthetized dog, which was processed with thoracotomy and ligated at the coronary artery, was significantly decreased by the safflor yellow injection and hydroxysafflor yellow A sodium 5 min-4 h after injection. The results are shown in Table 1.

TABLE 1 influence on ST segment elevation of anesthetized dog processed with thoracotomy after death caused by myocardial infarction

| Medicine | n | 5 min | 15 min | 30 min | 1 h | 2 h | 3 h | 4 h |
|---|---|---|---|---|---|---|---|---|
| Saline | 6 | 1.39 ± 0.22 | 1.55 ± 0.41 | 1.49 ± 0.32 | 1.55 ± 0.41 | 1.47 ± 0.41 | 1.32 ± 0.23 | 1.28 ± 0.22 |
| Safflor yellow | 6 | 0.87 ± 0.43 | 1.02 ± 0.46* | 0.88 ± 0.42* | 0.79 ± 0.42** | 0.87 ± 0.30* | 0.76 ± 0.42* | 0.79 ± 0.34* |
| Hydroxysafflor yellow A sodium | 6 | 0.84 ± 0.34* | 0.81 ± 0.29* | 0.78 ± 0.56* | 0.72 ± 0.36* | 0.61 ± 0.51* | 0.48 ± 0.40* | 0.33 ± 0.42** | b) the safflor yellow injection and the hydroxysafflor yellow A sodium were both able to significantly decrease the myocardial infarction range of the anesthetized dog processed with thoracotomy which was dead because of acute myocardial infarction, wherein a performance of the hydroxysafflor yellow A sodium was the best. The results are shown in Table 2.

TABLE 2 influence on acute myocardial infarction range of dog

| Medicine | n | Weight of myocardium (g) | Dangerous area (g) | Infarcted area (g) | Infarction rate % |
|---|---|---|---|---|---|
| Saline | 9 | 72 ± 18.1 | 12.0 ± 1.9 | 5.2 ± 1.6 | 42.5 ± 10.5 |
| Safflor yellow | 6 | 80.3 ± 11.3 | 17.5 ± 3.8** | 4.1 ± 1.8 | 25.3 ± 12.3** |
| Hydroxysafflor yellow A sodium | 6 | 73.2 ± 9.5 | 13.1 ± 3.8 | 2.2 ± 0.3 | 18.1 ± 5.8* | wherein *p<0.05, p<0.01, *p<0.001 vs the saline group.

Conclusion

Compared to the safflor yellow infection, the hydroxysafflor yellow A sodium had a better effect on preventing myocardial ischemic necrosis.

Pharmacodynamics Experiment 2:

Effects of hydroxysafflor yellow A sodium on presenting platelet aggregation and Acute cerebral ischemia.

Medicine Tested:

freeze-dried powder of the hydroxysafflor yellow A sodium (prepared in the preferred embodiment 1).

Experiment Content a) selectivity of heart and cerebral vessels isolated from the dog: fixing a cerebral basilar artery and a coronary artery ring of a Beagle dog on an isolated vascular measurement device, adjusting tension sensor and adding lemon phenylephrine to a liquid bath cup for maintaining proper vessel tension, then adding the hydroxysafflor yellow A sodium injection to the liquid bath cup once every 5 min with a dosage of 10 mg/ml until a vascular ring showed very weak response or no response (generally, the medicine was feed 4~5 times); calculating a vascular systolic or diastolic change value; wherein experimental results indicate that a relaxation effect of the hydroxysafflor yellow A sodium injection on a cardiac vascular ring was 30.9%, while a relaxation effect on a cerebral vascular ring was 72.8%; which means that the hydroxysafflor yellow A sodium injection has sufficient selectivity and relaxation function on the cerebral vascular.

b) influence on acute cerebral ischemia: utilizing SD rats, providing a cerebral ischemia model by middle cerebral artery occlusion (MCAO) suture method after intravenous injection with hydroxysafflor yellow A sodium; judging neurological behavior after feeding for 24 h, then cutting a head and taking a brain out, putting into a mould and cutting into 7 pieces, dyeing with TTC in such a manner that survival cerebral tissues were dyed red, and necrotic cerebral tissues were not dyed; calculating a ratio of the necrotic cerebral tissue and a cerebral hemisphere by a graphic analysis software; wherein results indicated that a cerebral infarction area of a solvent control group was 38%, and a cerebral infarction area of a nimodipine positive control group was 15.4%; cerebral infarction areas of hydroxysafflor yellow A sodium injection low, medium and high dosage groups were respectively 38%, 27.2% and 21.5%; compared to the solvent control group, medium and high dosage groups had significant effects on reducing cerebral tissue necrosis caused by the acute cerebral ischemia.

c) influence on cerebral vascular permeability of the rats: intravenously injecting the rat once a day for 7 consecutive days, anesthetizing the rat after the last injection, intravenously injecting Evans blue with a dosage of 50 mg/kg, ligating bilateral common carotid arteries after 5 minutes, cutting a head after 3 hours and taking a brain out, immersing in a formamide solution after weighing, putting in an incubator with a temperature of 45° C. for 72 h, in such a manner that the Evans blue in the cerebral vessel was leached to the formamide solution, detecting an amount of the Evans blue in the formamide solution by a spectrophotometer, wherein the amount indicated a level of the cerebral vascular permeability; wherein experimental results showed that the hydroxysafflor yellow A sodium injection medium and high dosage groups had significant effects on reducing the Evans blue leached from the cerebral vascular, which means the medicine has a sufficient effect on reducing the vascular permeability.

d) influence on cerebral blood flow: utilizing Beagle dogs as experimental animals, anesthetizing with pentobarbital sodium before isolating an external jugular vein, an internal jugular vein and a vertebral artery, ligating the external jugular vein, placing a flow sensors in the internal jugular vein and the vertebral artery, adding the blood flows recorded by the two sensors together and multiplying by 2 for representing blood supply of a whole brain, taking the brain out after the experiment for weighing and calculating the blood flow per 100 g cerebral tissue; wherein experimental results showed that the hydroxysafflor yellow A sodium injection has an effect of increasing the blood flow on the medium and high dosage groups after intravenous injection, but a maintaining time thereof was short (about 15 min); the experiment suggested that intravenous injection should be apply for clinically treating acute cerebral ischemia.

e) influence on acute cerebral hypoxia: utilizing Kunming mice and the SD rats for the experiment, putting the animals in a hypoxic environment, recording a survival time, observing whether a tolerance of the acute hypoxia of the animal was increased after feeding the medicine; wherein experimental results showed that for the mice in a sealed container, the survival time of the solvent control group was 32 min and the survival times of the hydroxysafflor yellow injection low, medium and high dosage groups were 37 min, 37 min and 37 min; statistical results indicated a significant difference (P<0.05~0.01) according to the solvent control group; the rat experiment was provided in an environment with 97% nitrogen and 3% oxygen; time counting started when the animal was put into the container and stoped when the animal was out of breath, an average survival time of the solvent control group was 3 minutes and 43 seconds and a survival time of the positive control group (nimodipine) was 5 minutes and 45 seconds, a difference therebetween was significant; survival times of the hydroxysafflor yellow A sodium injection low, medium and high dosage groups were 3 minutes and 30 seconds, 4 minutes and 35 seconds, and 4 minutes and 12 seconds; and a significant survival time difference existed between the solvent control group and the medium and high dosage groups.

f) preventing platelet accumulation: the experiment comprises instrument detection and in vivo detection:

1) the instrument detection method: intravenously injecting hydroxysafflor yellow A sodium in a rabbit once a day for 5 consecutive days, collecting 4 ml heart blood within 2 h after the last injection, centrifuging with a low speed for obtaining a platelet-rich blood serum; centrifuging with a high speed for obtaining a platelet-poor blood serum, utilizing adenosine diphosphate (ADP) and platelet activating factor (PAF) as platelet accumulation derivant, and testing with a platelet aggregation analyzer; wherein the platelet aggregation experiment of hydroxysafflor yellow A sodium injection on preventing the platelet aggregation induced by the ADP and the PAF indicated a sufficient effect on presenting the platelet aggregation, and a positive quantity-effect relationship existed between the three dosage groups; and 2) the in vivo detection method: forming a short circuit between a artery and a vein of the rat with a latex tube, fixing a operation silk in the latex tube; with platelet adhesion, opening the short circuit in such manner that the blood flows cross the artery and the vein through the latex tube for 15 minutes, then taking the silk out for weighing, subtracting a dry weight of the silk for obtaining a weight of the platelet; wherein the experimental results showed that the weight of the platelet adhered of the solvent control group was 14.8±1.57 mg, the weight of the positive control group was 8.62±2.79 mg, and the weights of the hydroxysafflor yellow A sodium low, medium and high dosage groups were 13.8±1.95 mg, 9.87±1.50 mg and 9.02±1.29 mg; a significant difference existed according to the medium, high dosage groups and the solvent control group, which indicated a sufficient effect of the hydroxysafflor yellow A sodium injection on preventing platelet aggregation of the rat.

g) influence on blood viscosity: processing a rabbit with intravenous injection once a day for 5 consecutive days, directly detecting heart blood processed with anticoagulant by a blood rheometer 2 hour after the last injection; wherein results showed that, compared to the solvent control group, low-cut, medium-cut and high-cut, which were indexes of the blood viscosity, were decreased with increase of the dosage of the hydroxysafflor yellow A sodium groups; the effect of the high dosage group was better than the positive control nimodipine injection group, which indicated that the hydroxysafflor yellow A sodium injection has a sufficient effect on decreasing blood viscosity.

Stability Experiment

Object: observing stability of the hydroxysafflor yellow A sodium as shown in the formula (I) and the hydroxysafflor yellow A, and physical and chemical data thereof.

Medicine Tested:

The hydroxysafflor yellow A prepared according to the Chinese patent CN102675379A, wherein a purity thereof was 89.9%.

The hydroxysafflor yellow A sodium (prepared in the preferred embodiment 1) with a purity of 98.6%.

Experimental results are shown in Table 3.

TABLE 3 experimental result of stability of hydroxysafflor yellow A sodium

| Event | | Accelerated for 0 month | Accelerated for 1 month | Accelerated for 2 months | Accelerated for 3 months |
|---|---|---|---|---|---|
| Hydroxysafflor yellow A | Total impurity | 10.1% | 14.9% | 20.8% | 28.6% |
| | Content (counting Hydroxyl A) | 89.8% | 84.7% | 79.2% | 71.2% |

TABLE 3-continued experimental result of stability of hydroxysafflor yellow A sodium

| Event | | Accelerated for 0 month | Accelerated for 1 month | Accelerated for 2 months | Accelerated for 3 months |
|---|---|---|---|---|---|
| Hydroxysafflor yellow A sodium | Total impurity | 1.4% | 1.9% | 2.4% | 3.0% |
| | Content (counting Hydroxyl A) | 94.9% | 94.4% | 94.1% | 93.5% |

The hydroxysafflor yellow A prepared in the preferred embodiment 2 with acidizing, wherein a purity thereof was 99.2%.

The hydroxysafflor yellow A sodium (prepared in the preferred embodiment 1) with a purity of 99.2%.

Experimental results are shown in Table 4.

TABLE 4 experimental result of stability of hydroxysafflor yellow A sodium

| Event | | Accelerated for 0 month | Accelerated for 1 month | Accelerated for 2 months | Accelerated for 3 months |
|---|---|---|---|---|---|
| Hydroxysafflor yellow A | Total impurity | 0.8% | 5.9% | 10.7% | 18.6% |
| | Content (counting Hydroxyl A) | 99.1% | 94.1% | 89.2% | 81.3% |
| Hydroxysafflor yellow A sodium | Total impurity | 0.8% | 1.3% | 1.9% | 2.5% |
| | Content (counting Hydroxyl A) | 95.6% | 95.1% | 94.5% | 94.0% |

The physical and chemical data of the hydroxysafflor yellow A sodium are shown in Table 5.

TABLE 5 physical and chemical data of hydroxysafflor yellow A sodium

| Simple | PH | Solubility |
|---|---|---|
| Hydroxysafflor yellow A | 1.9 | Slightly soluble |
| Hydroxysafflor yellow A sodium | 5.8 | Easily soluble |

According to the experimental results, the comparison experiment of the hydroxysafflor yellow A sodium as shown in the formula (I) and the hydroxysafflor yellow A illustrates that the stability of the hydroxysafflor yellow A sodium was better, in such a manner that quality and safety thereof were better. Acidity of the hydroxysafflor yellow A was strong and was out of pH tolerance of human, which will lead to discomfort such as pain. Furthermore, solubility thereof was not sufficient. According to the present invention, the hydroxysafflor yellow A sodium has better tolerance and solubility.

A structure of the hydroxysafflor yellow A sodium compound prepared in the preferred embodiment 1 was identified by infrared spectrometry (IR), mass spectrometry (MS), hydrogen nuclear magnetic resonance spectrometry ($^1$H-NMR), carbon nuclear magnetic resonance spectrometry ($^{13}$C-NMR), COSY spectrometry, DEPT135 spectrometry and HSQC spectrometry, wherein the structure is shown as follows.

a) infrared absorption spectrum

Instruments: Bruker VECTOR-22 infrared absorption spectrograph; and

IR (compressed potassium bromide);

wherein main characteristic peaks of the IR spectrum are shown in Table 6.

TABLE 6 characteristic peaks of IR spectrum

| Absorption peak cm$^{-1}$ | Vibration type | Group | Strength |
| --- | --- | --- | --- |
| 3361 | $v_{-OH}$ | —OH | br s |
| 1650 | $v_{C=O}$ | —C=O | s |
| 1624 | $v_{C=C}$ | —C=C— | s |
| 1604 1515 | $v_{C=C}$ | $C_6H_6$ | s |
| 1440 | $\delta_{-CH2}$ | —CH$_2$ | m |
| 1171 1077 1005 | $v_{C-O}$ | —C—OH | s | b) mass spectrum

Instrument: LC-MS multistage ion trap mass spectrometry system (LCQ-DECAXP) of America FINNIGAN company.

Test condition: ESI

The mass spectrum:

+c ESI 635.14 (M)$^+$

−c ESI 611.25 (M-Na)$^-$ c) hydrogen nuclear magnetic resonance spectrum and carbon spectrum Instrument: BRUCKER AVANCE III 500 superconducting NMR spectrometer.

Test condition: solution: DMSO, interior label: TMS.

The nuclear magnetic resonance $^1$H-NMR (FIG. 1), $^{13}$C-NMR (FIG. 2), COSY spectrum (FIG. 3), DEPT135 spectrum (FIG. 4) and HSQC spectrum (FIG. 5) of the hydroxysafflor yellow A sodium as shown in the formula (I) are illustrated by drawings.

Figure 1:
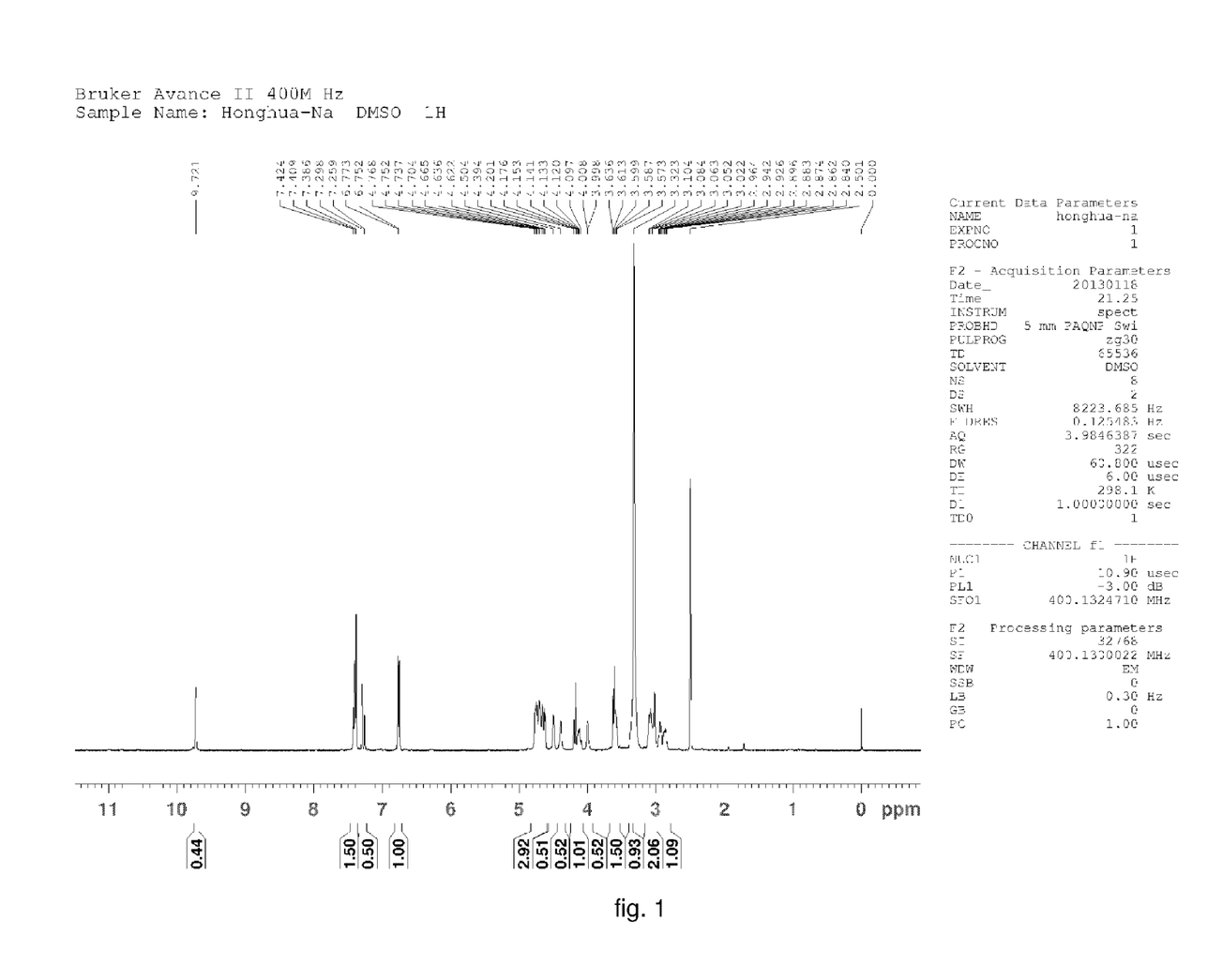
FIG. 1 is a hydrogen spectrum of hydroxysafflor yellow A sodium as shown in the formula (I) according to the present invention.

$^1$H-NMR data of the hydroxysafflor yellow A sodium as shown in the formula (I) are as follows.

According to chemical shifts δ (ppm), 2.84~4.14 (14H) belong to a sugar moiety hydrogen G1~G6 and G'1~G'6; 4.39~4.77 (8H) belong to sugar hydroxyl hydrogen; 7.26 (1H) and 7.39 (1H) belong to 8 and 9; 6.75~7.42 (4H) belong to 11~15; 18.65 (1H) belongs to 3-OH; 4.70 (1H) belongs to 4-OH; and 9.72 (1H) belongs to 13-OH.

Figure 2:
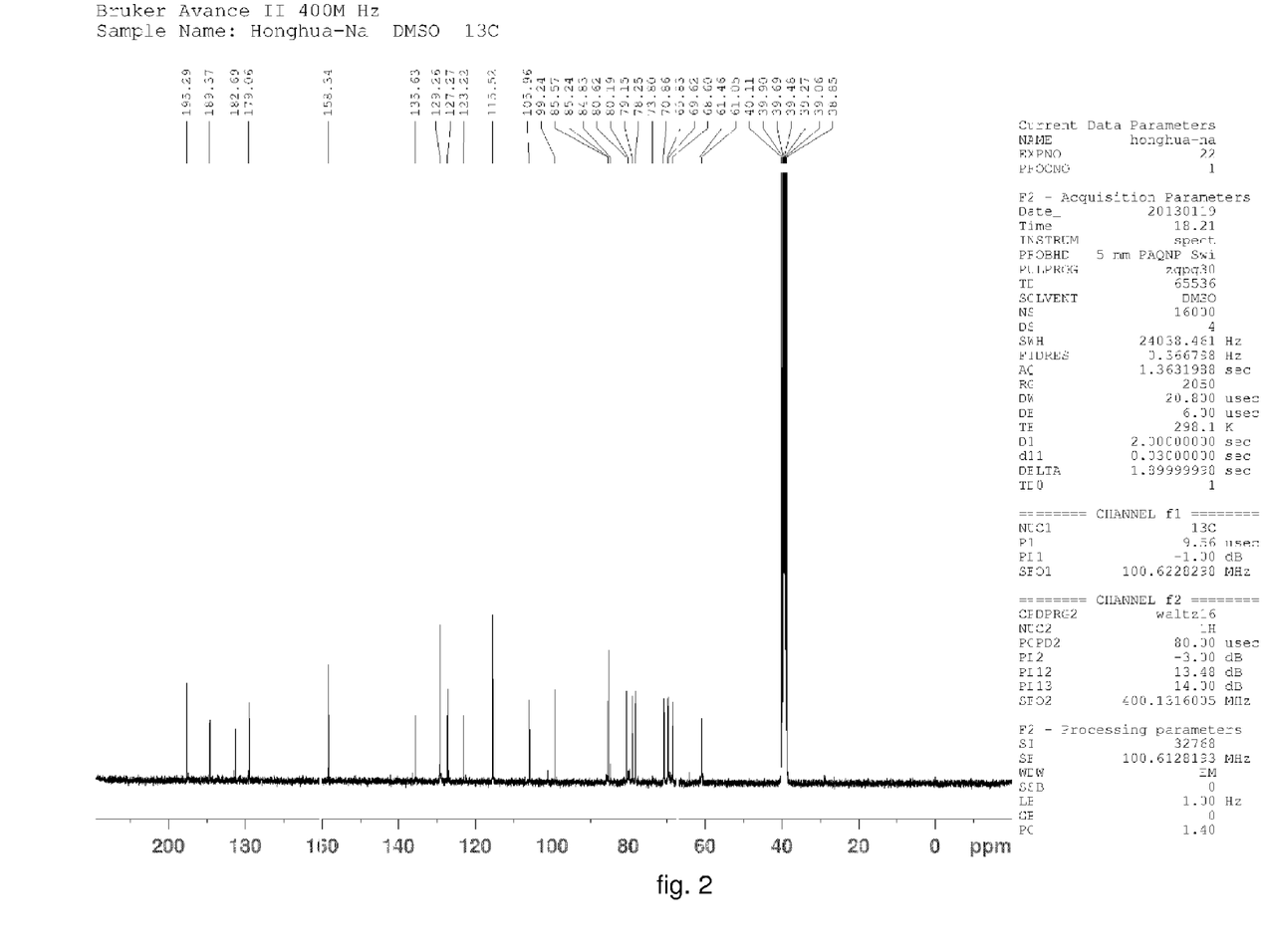
FIG. 2 is a carbon spectrum of the hydroxysafflor yellow A sodium as shown in the formula (I) according to the present invention.
Figure 3:
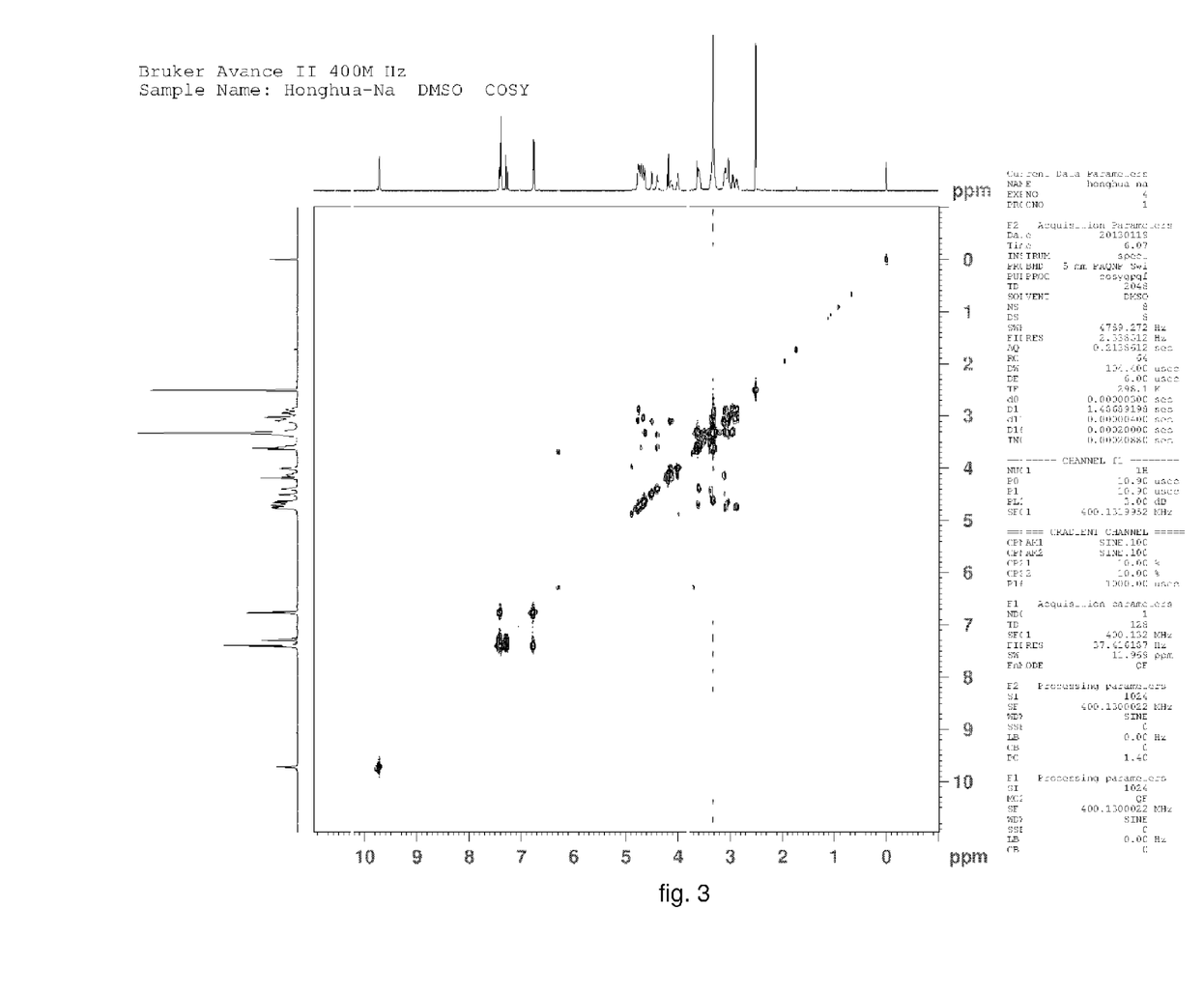
FIG. 3 is a COSY spectrum of the hydroxysafflor yellow A sodium as shown in the formula (I) according to the present invention.

$^{13}$C-NMR data of the hydroxysafflor yellow A sodium as shown in the formula (I) are as follows.

Figure 4:
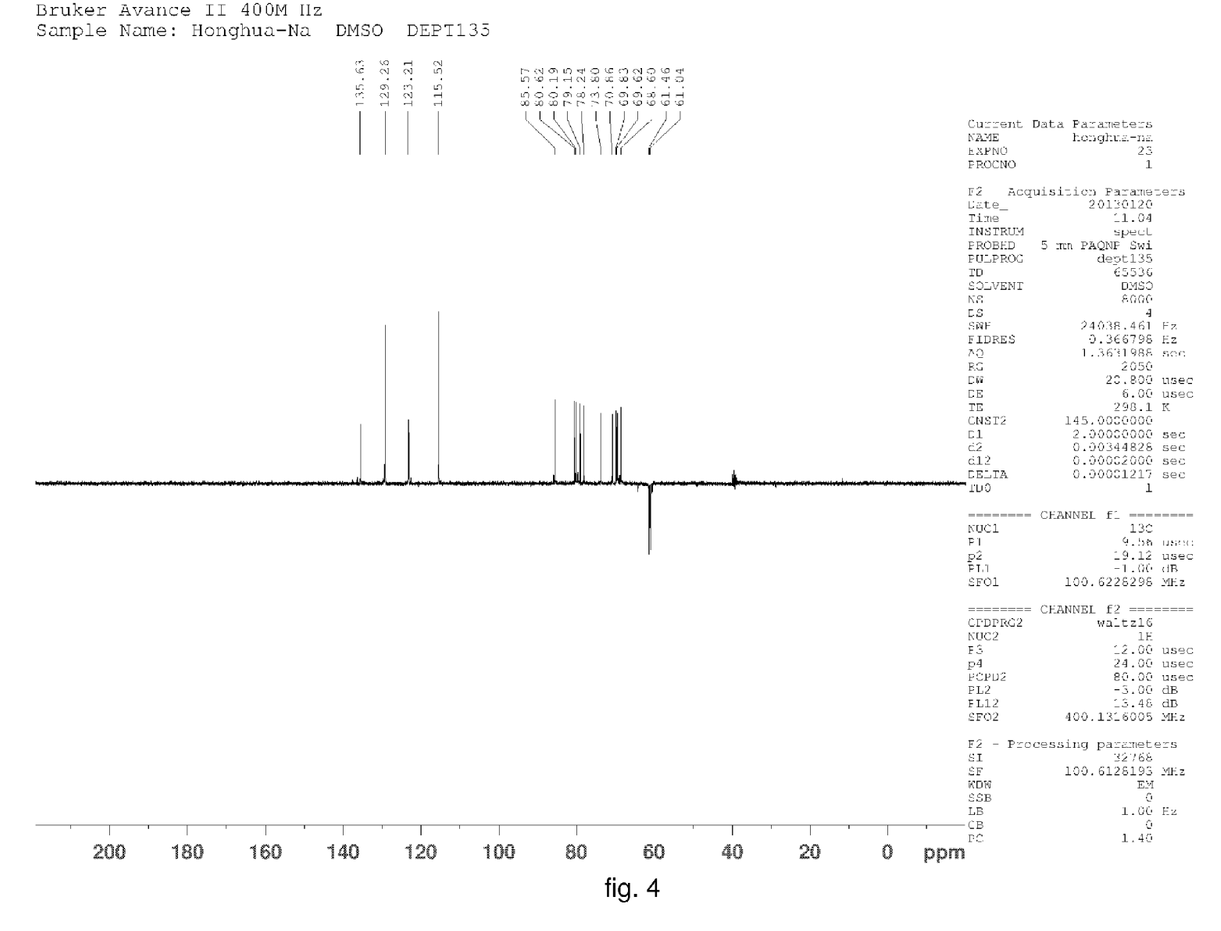
FIG. 4 is a DEPT135 spectrum of the hydroxysafflor yellow A sodium as shown in the formula (I) according to the present invention.
Figure 5:
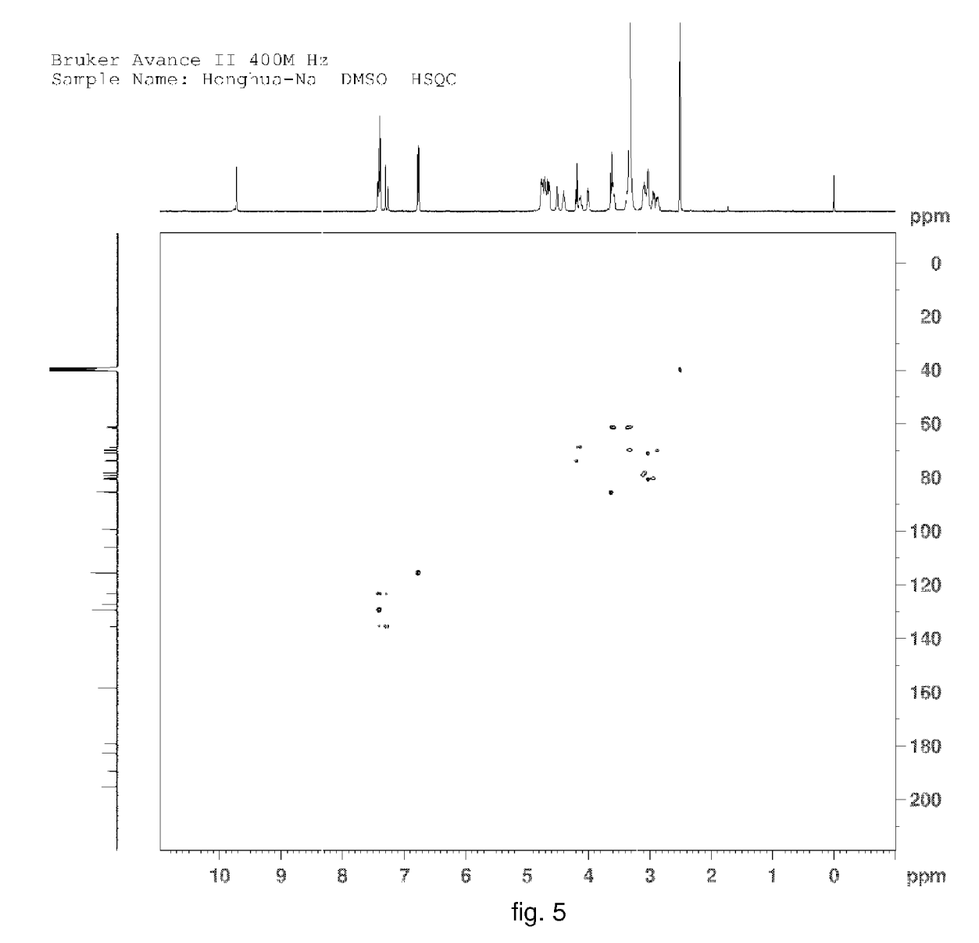
FIG. 5 is an HSQC spectrum of the hydroxysafflor yellow A sodium as shown in the formula (I) according to the present invention.

According to chemical shifts δ (ppm) of the DEPT135, 61.05 (1C) and 61.46 (1C) (secondary carbon) belong to sugar moiety carbon G6 and G'6; 68.60, 69.62, 69.83, 70.86, 73.80, 78.25, 79.15, 80.19, 80.62, and 85.57 (10C) (tertiary carbon) belong to the sugar moiety carbon G1~G5 and G'1~G'5; 115.52 (2C) (tertiary carbon) belongs to 12 and 14; 129.26 (2C) (tertiary carbon) belongs to 11 and 15; 123.22 (1C) and 135.63 (1C) (tertiary carbon) belong to 8 and 9; the chemical shift (PPM) 189.37, 105.96, 195.29, 85.24, 182.69 and 99.24 (6C) belong to 1~6; 179.06 (1C), 127.27 (1C) and 158.34 (1C) respectively belong to 7, 10 and 13.

These and other objectives, features, and advantages of the present invention will become apparent from the following detailed description, the accompanying drawings, and the appended claims.

DETAILED DESCRIPTION OF THE PREFERRED EMBODIMENT

Preferred Embodiment 1

Hydroxysafflor Yellow A Sodium

Weighting safflower, adding deionized water, wherein a weight of the deionized water was 12.5 times of a weight of the safflower, extracting at 100° C. for 20~25 min, then filtering, adding the deionized water into residue and extracting again with the above condition, wherein a weight of the deionized water was 10 times of the weight of the safflower, then filtering; mixing filtrate, cooling to a room temperature, processing with centrifugation by a centrifugal machine, collecting centrifugate for further utilization; slowly adding the above centrifugate to balanced 001*7 sodion-exchange resin, wherein a ratio of a diameter and a height of a resin column was 1:10, a volume thereof was 500 ml, a flow rate thereof was 3 ml/min; then discharging extract from the column with water, wherein a volume of the water equals to the volume of the column; collecting liquid flowed out which comprises the hydroxysafflor yellow A sodium, slowly adding to a macroporous adsorption resin (HZ801) separation column, wherein a ratio of a diameter and a height thereof was 1:12, a sampling flow rate was 10 ml/min; eluting with the deionized water at the room temperature after sampling, wherein a eluting flow rate was 20 ml/min; processing eluant with vacuum concentration at 60° C. for obtaining a concentrated crude product of the hydroxysafflor yellow A sodium; wherein judging from the safflower, 1 kg the safflower was able to prepare 100 ml concentrate; passing the concentrated crude product of the hydroxysafflor yellow A sodium through a dextran gel LH-20 column, wherein a ratio of a diameter and a height thereof was 1:5, a sampling volume was 10% of a volume of a column holder, pure water was utilized as an eluting agent, an eluting flow rate was 5 ml/min; collecting liquid comprising the hydroxysafflor yellow A sodium; processing the collected liquid with vacuum concentration at 60° C. for obtaining a concentrated refined product of the hydroxysafflor yellow A sodium, wherein judging from the safflower, 1 kg the safflower was able to prepare 35~50 ml concentrate; freeze-drying for obtaining a refined powder of the hydroxysafflor yellow A sodium which was pale yellow, wherein a purity thereof was 98.6%, a yield thereof was 0.45% judging from the safflower.

Dissolving the hydroxysafflor yellow A sodium prepared above in injection water, packing in bottles after filtered by a 0.22 μm macroporous filtering membrane, then freeze-drying for obtaining a freeze-dried injection of the hydroxysafflor yellow A sodium.

Preferred Embodiment 2

Hydroxysafflor Yellow A Sodium

Weighting safflower, adding deionized water, wherein a weight of the deionized water was 12.5 times of a weight of the safflower, extracting at 100° C. for 20~25 min, then filtering, adding the deionized water into residue and extracting again with the above condition, wherein a weight of the deionized water was 10 times of the weight of the safflower, then filtering; mixing filtrate, cooling to a room temperature, processing with centrifugation by a centrifugal machine, collecting centrifugate for further utilization; slowly adding to a macroporous adsorption resin (HZ801) separation column, wherein a ratio of a diameter and a height thereof was 1:12, a sampling flow rate was 10 ml/min; eluting with the deionized water at the room temperature after sampling, wherein a eluting flow rate was 20 ml/min; processing eluant with vacuum concentration at 60° C. for obtaining a concentrated crude product of safflor yellow; wherein judging from the safflower, 1 kg the safflower was able to prepare 100 ml concentrate; passing the concentrated crude product of the safflor yellow through a dextran gel LH-20 column, wherein a ratio of a diameter and a height thereof was 1:5, a sampling volume was 10% of a volume of a column holder, pure water was utilized as an eluting agent, an eluting flow rate was 5 ml/min; collecting liquid comprising the safflor yellow; processing the collected liquid with vacuum concentration at 60° C. for obtaining safflor yellow concentrate, wherein judging from the safflower, 1 kg the safflower was able to prepare 35~50 ml concentrate; freeze-drying for obtaining a powder of the safflor yellow which was pale yellow, wherein a purity thereof was 90%; adding water to the safflor yellow powder before acidizing with HCl, placing at a cool place for 2~24 h until solid was separated out; filtering the solid before adding water, then adjusting the pH value to 6.0 with 0.1 mol/L~10 mol/L sodium hydroxide, freeze-drying filtrate for obtaining a refined product of the hydroxysafflor yellow A sodium which was pale yellow, wherein a purity thereof was 99.2%, a yield thereof was 0.70% judging from the safflower.

According to identification, a structure of the hydroxysafflor yellow A sodium was as shown in the formula (I).

Dissolving the refined product of the hydroxysafflor yellow A sodium prepared above in injection water, packing in bottles after filtered by an ultrafiltration membrane with molecular weight cut-off of 8000~10000 daltons, then freeze-drying for obtaining a freeze-dried injection of the hydroxysafflor yellow A sodium.

Preferred Embodiment 3

Hydroxysafflor Yellow A Sodium

Weighting safflower, adding deionized water, wherein a weight of the deionized water was 12.5 times of a weight of the safflower, extracting at 100° C. for 20~25 min, then filtering, adding the deionized water into residue and extracting again with the above condition, wherein a weight of the deionized water was 10 times of the weight of the safflower, then filtering; mixing filtrate, cooling to a room temperature, processing with centrifugation by a centrifugal machine, collecting centrifugate for further utilization; slowly adding the above centrifugate to balanced 001*7 sodion-exchange resin, wherein a ratio of a diameter and a height of a resin column was 1:10, a volume thereof was 500 ml, a flow rate thereof was 3 ml/min; slowly adding to a macroporous adsorption resin (HZ801) separation column, wherein a ratio of a diameter and a height thereof was 1:12, a sampling flow rate was 10 ml/min; eluting with the deionized water at the room temperature after sampling, wherein a eluting flow rate was 20 ml/min; processing eluant with vacuum concentration at 60° C. for obtaining a concentrated crude product of hydroxysafflor yellow A sodium; wherein judging from the safflower, 1 kg the safflower was able to prepare 100 ml concentrate; passing the concentrated crude product of the hydroxysafflor yellow A sodium through a dextran gel LH-20 column, wherein a ratio of a diameter and a height thereof was 1:5, a sampling volume was 10% of a volume of a column holder, pure water was utilized as an eluting agent, an eluting flow rate was 5 ml/min; collecting liquid comprising the hydroxysafflor yellow A sodium; processing the collected liquid with vacuum concentration at 60° C. for obtaining a concentrated refined product of the hydroxysafflor yellow A sodium, wherein judging from the safflower, 1 kg the safflower was able to prepare 35~50 ml concentrate; freeze-drying filtrate for obtaining a refined product of the hydroxysafflor yellow A sodium which was pale yellow, wherein a purity thereof was 98.7%, a yield thereof was 0.50% judging from the safflower.

According to identification, a structure of the hydroxysafflor yellow A sodium was as shown in the formula (I).

Preferred Embodiment 4

Hydroxysafflor Yellow A Sodium

Weighting safflower, adding deionized water, wherein a weight of the deionized water was 12.5 times of a weight of the safflower, extracting at 100° C. for 20~25 min, then filtering, adding the deionized water into residue and extracting again with the above condition, wherein a weight of the deionized water was 10 times of the weight of the safflower, then filtering; mixing filtrate, cooling to a room temperature, processing with centrifugation by a centrifugal machine, collecting centrifugate for further utilization; slowly adding to a macroporous adsorption resin (HZ801) separation column, wherein a ratio of a diameter and a height thereof was 1:12, a sampling flow rate was 10 ml/min; eluting with the deionized water at the room temperature after sampling, wherein a eluting flow rate was 20 ml/min; processing eluant with vacuum concentration at 60° C. for obtaining a concentrated crude product of safflor yellow; wherein judging from the safflower, 1 kg the safflower was able to prepare 100 ml concentrate; passing the concentrated crude product of the safflor yellow through a dextran gel LH-20 column, wherein a ratio of a diameter and a height thereof was 1:5, a sampling volume was 10% of a volume of a column holder, pure water was utilized as an eluting agent, an eluting flow rate was 5 ml/min; collecting liquid comprising the safflor yellow; processing the collected liquid with vacuum concentration at 60° C. for obtaining safflor yellow concentrate, wherein judging from the safflower, 1 kg the safflower was able to prepare 35~50 ml concentrate; freeze-drying for obtaining a powder of the safflor yellow which was pale yellow, wherein a purity thereof was 90%; adding water to the safflor yellow powder before acidizing with HCl, placing at a cool place for 2~24 h until solid was separated out; filtering the solid before adding water, then adjusting the pH value to 6.0 with 0.1 mol/L~10 mol/L sodium hydroxide, freeze-drying filtrate for obtaining a refined product of the hydroxysafflor yellow A sodium which was pale yellow, wherein a purity thereof was 99.1%, a yield thereof was 0.75% judging from the safflower.

According to identification, a structure of the hydroxysafflor yellow A sodium was as shown in the formula (I).

Preferred Embodiment 5

Hydroxysafflor Yellow A Sodium

Weighting safflower, adding deionized water, wherein a weight of the deionized water was 12.5 times of a weight of the safflower, extracting at 100° C. for 20~25 min, then filtering, adding the deionized water into residue and extracting again with the above condition, wherein a weight of the deionized water was 10 times of the weight of the safflower, then filtering; mixing filtrate, cooling to a room temperature, processing with centrifugation by a centrifugal machine, collecting centrifugate for further utilization; slowly adding to a macroporous adsorption resin (HZ801) separation column, wherein a ratio of a diameter and a height thereof was 1:12, a sampling flow rate was 10 ml/min; eluting with the deionized water at the room temperature after sampling, wherein a eluting flow rate was 20 ml/min; processing eluant with vacuum concentration at 60° C. for obtaining a concentrated crude product of safflor yellow; wherein judging from the safflower, 1 kg the safflower was able to prepare 100 ml concentrate; passing the concentrated crude product of the safflor yellow through a dextran gel LH-20 column, wherein a ratio of a diameter and a height thereof was 1:5, a sampling volume was 10% of a volume of a column holder, pure water was utilized as an eluting agent, an eluting flow rate was 5 ml/min; collecting liquid comprising the safflor yellow; processing the collected liquid with vacuum concentration at 60° C. for obtaining safflor yellow concentrate, wherein judging from the safflower, 1 kg the safflower was able to prepare 35~50 ml concentrate; freeze-drying for obtaining a powder of the safflor yellow which was pale yellow, wherein a purity thereof was 90%; adding water to the safflor yellow powder before acidizing with HCl, placing at a cool place for 2~24 h until solid was separated out; filtering the solid before adding water, then adjusting the pH value to 6.0 with 0.1 mol/L~10 mol/L sodium hydroxide, freeze-drying filtrate for obtaining a refined product of the hydroxysafflor yellow A sodium which was pale yellow, wherein a purity thereof was 99.3%, a yield thereof was 0.69% judging from the safflower.

According to identification, a structure of the hydroxysafflor yellow A sodium was as shown in the formula (I).

Preferred Embodiment 6

Hydroxysafflor Yellow A Sodium

Weighting safflower, adding deionized water, wherein a weight of the deionized water was 12.5 times of a weight of the safflower, extracting at 100° C. for 20~25 min, then filtering, adding the deionized water into residue and extracting again with the above condition, wherein a weight of the deionized water was 10 times of the weight of the safflower, then filtering; mixing filtrate, cooling to a room temperature, processing with centrifugation by a centrifugal machine, collecting centrifugate for further utilization; slowly adding to a macroporous adsorption resin (HZ801) separation column, wherein a ratio of a diameter and a height thereof was 1:12, a sampling flow rate was 10 ml/min; eluting with the deionized water at the room temperature after sampling, wherein a eluting flow rate was 20 ml/min; processing eluant with vacuum concentration at 60° C. for obtaining a concentrated crude product of safflor yellow; wherein judging from the safflower, 1 kg the safflower was able to prepare 100 ml concentrate; passing the concentrated crude product of the safflor yellow through a dextran gel LH-20 column, wherein a ratio of a diameter and a height thereof was 1:5, a sampling volume was 10% of a volume of a column holder, pure water was utilized as an eluting agent, an eluting flow rate was 5 ml/min; collecting liquid comprising the safflor yellow; adding the collected liquid to balanced strongly acidic H cat-ionic-exchange resin and collecting liquid flowed out; processing the collected liquid with vacuum concentration at 60° C. for obtaining hydroxysafflor yellow A concentrate, placing at a cool place for 2~24 h until solid was separated out; filtering the solid before adding water, then adjusting the pH value to 6.0 with 0.1 mol/L~10 mol/L sodium hydroxide, freeze-drying filtrate for obtaining a refined product of the hydroxysafflor yellow A sodium which was pale yellow, wherein a purity thereof was 99.8%, a yield thereof was 0.68% judging from the safflower.

According to identification, a structure of the hydroxysafflor yellow A sodium was as shown in the formula (I).

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A hydroxysafflor yellow A sodium, as shown in a formula (I);

2. A method for preparing hydroxysafflor yellow A sodium as recited in claim 1 and shown in the formula (I), comprising a step of preparing the hydroxysafflor yellow A sodium as shown in the formula (I) with hydroxysafflor yellow A as shown in a formula (II);

wherein the hydroxysafflor yellow A sodium as shown in the formula (I) is prepared with the hydroxysafflor yellow A as shown in the formula (II) by a method comprising a step of: preparing the hydroxysafflor yellow A sodium as shown in the formula (I) with the hydroxysafflor yellow A as shown in the formula (II) by sodion-exchange resin column, or by reaction with a sodium salt; wherein the sodium salt is selected from the group consisting of sodium hydroxide, sodium carbonate and sodium bicarbonate.

3. The method, as recited in claim 2, wherein the sodion-exchange resin is 001*7 sodion-exchange resin or macroporous HB-8 sodion-exchange resin.

4. The method, as recited in claim 2, wherein safflower is utilized as a raw material, the hydroxysafflor yellow A sodium is obtained after extraction, sodium salt transformation, separation and purification, wherein the method particularly comprises steps of:
   a) extracting: extracting the safflower with water for obtaining extract thereof;
   b) transforming to sodium salt: passing the extract obtained in the step a) through a sodion-exchange resin column, transforming safflor yellow to the hydroxysafflor yellow A sodium as shown in the formula (I), obtaining eluant comprising the hydroxysafflor yellow A sodium as shown in the formula (I);
   c) separating: separating the eluant obtained in the step b), which comprises the hydroxysafflor yellow A sodium as shown in the formula (I), by a macroporous adsorbent resin column, obtaining a crude product of the hydroxysafflor yellow A sodium as shown in the formula (I); and
   d) purifying: separating the crude product obtained in the step c) of the hydroxysafflor yellow A sodium as shown in the formula (I) by dextran gel column chromatography, then filtering with an ultrafiltration membrane, obtaining a refined product of the hydroxysafflor yellow A sodium as shown in the formula (I).

5. The method, as recited in claim 2, wherein safflower is utilized as a raw material, the hydroxysafflor yellow A sodium is obtained after extraction, separation, purification, acidization and sodium salt transformation, wherein the method particularly comprises steps of:
   a) extracting: extracting the safflower with water for obtaining extract thereof;
   b) separating: separating the eluant of the safflower obtained in the step a) by a macroporous adsorbent resin column, obtaining a crude product of the safflor yellow;
   c) purifying: separating the crude product of the safflor yellow obtained in the step b) by dextran gel column chromatography, then filtering with an ultrafiltration membrane, freeze-drying for obtaining a refined product of the safflor yellow;
   d) acidizing: adding water to the refined product of the safflor yellow, adding acid for adjusting a pH value to 1.5~2.5, collecting pale yellow solid separated out for obtaining hydroxysafflor yellow A as shown in the formula (II); and
   e) transforming to sodium salt: adding water to the hydroxysafflor yellow A obtained in the step d), which is shown in the formula (II), and adjusting the pH value to 6 with 0.1 mol/L~10 mol/L sodium hydroxide, sodium carbonate or sodium bicarbonate (preferably sodium hydroxide), transforming the hydroxysafflor yellow A as shown in the formula (II) to the hydroxysafflor yellow A sodium as shown in the formula (I), filtering with an ultrafiltration membrane, and freeze-drying filtrate for obtaining a refined product of the hydroxysafflor yellow A sodium as shown in the formula (I).

6. The method, as recited in claim 4, wherein the macroporous adsorbent resin is HSZ801 macroporous adsorbent resin.

7. The method, as recited in claim 5, wherein the macroporous adsorbent resin is HSZ801 macroporous adsorbent resin.

8. The method, as recited in claim 4, wherein the dextran gel column chromatography comprises Sephadex LH-20 dextran gel column chromatography for separating, and pure water as an eluting agent; an ultrafiltration membrane with molecular weight cut-off of 8000~10000 daltons for ultrafiltering.

9. The method, as recited in claim 5, wherein the dextran gel column chromatography comprises Sephadex LH-20 dextran gel column chromatography for separating, and pure water as an eluting agent; an ultrafiltration membrane with molecular weight cut-off of 8000~10000 daltons for ultrafiltering.

10. A pharmaceutic preparation, comprising hydroxysafflor yellow A sodium as recited in claim 1 and shown in the formula (I) as an active ingredient and a pharmaceutically acceptable carrier.

11. The pharmaceutic preparation, as recited in claim 10, wherein said pharmaceutic preparation is a freeze-dried injection.

12. The pharmaceutic preparation, as recited in claim 11, wherein said pharmaceutic preparation is prepared by a method comprising steps of: dissolving the hydroxysafflor yellow A sodium as recited in claim 1 and shown in the formula (I) in injection water, then packing in bottles after filtered by a 0.22 μm macroporous filtering membrane or a ultrafiltration membrane with molecular weight cut-off of 8000~10000 daltons, and freeze-drying for obtaining the freeze-dried injection of the hydroxysafflor yellow A sodium as shown in the formula (I).

13. A method for treating a disease caused by myocardial ischemia, cerebral ischemia or thrombosis in a subject, comprising: applying a therapeutically effective amount of the hydroxysafflor yellow A sodium, as recited in claim 1 and shown in the formula (I), to the subject.

* * * * *